United States Patent [19]

Nowotnik et al.

[11] Patent Number: 4,818,813
[45] Date of Patent: Apr. 4, 1989

[54] COMPLEXES OF TECHNETIUM 99M WITH PROPYLENE AMINE OXIMES

[75] Inventors: David P. Nowotnik; Lewis R. Canning, both of Bucks, England

[73] Assignee: Amersham International plc., Bucks, England

[21] Appl. No.: 122,507

[22] Filed: Nov. 18, 1987

Related U.S. Application Data

[63] Continuation of Ser. No. 791,995, Oct. 23, 1985, abandoned.

[30] Foreign Application Priority Data

Oct. 24, 1984 [GB] United Kingdom ................. 8426845

[51] Int. Cl.$^4$ .................... A61K 49/02; C07C 131/00; C07D 295/12; C07F 13/00
[52] U.S. Cl. ....................................... 534/14; 424/1.1; 564/253
[58] Field of Search ........................... 534/14; 424/1.1; 564/253

[56] References Cited

U.S. PATENT DOCUMENTS

| | | | |
|---|---|---|---|
| 4,374,821 | 2/1983 | Glavan et al. | 534/14 X |
| 4,444,690 | 4/1984 | Fritzberg | 534/14 |
| 4,605,758 | 8/1986 | Schloemer | 562/418 |
| 4,615,876 | 10/1986 | Troutner et al. | 534/14 |

FOREIGN PATENT DOCUMENTS 0123504 10/1984 European Pat. Off. ............. 534/14

Primary Examiner—John F. Terapane
Assistant Examiner—Virginia Caress
Attorney, Agent, or Firm—Wenderoth, Lind & Ponack

[57] ABSTRACT

Novel propylene amine oxime ligands have the formula

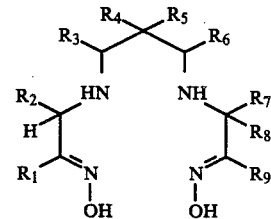

where each of $R_1$, $R_2$, $R_3$, $R_4$, $R_5$, $R_6$, $R_7$ or $R_8$ may be hydrogen, hydrocarbon, carboxyl, amine, amide or nitrile, provided that, if $R_1$ is the same as $R_9$ and $R_2$ is the same as $R_7$, then $R_8$ is not H. These unsymmetrical ligands form complexes with Technetium-99m which are capable, on injection into mammals, of crossing the blood-brain barrier and of being retained in the brain for a time to permit diagnosis.

2 Claims, No Drawings

COMPLEXES OF TECHNETIUM 99M WITH PROPYLENE AMINE OXIMES

This application is a continuation of now abandoned application Ser. No. 791,995, filed Oct. 23, 1985.

Technetium-99m (Tc-99m) is the favoured radionuclide for organ imaging and other forms of in vivo diagnosis. Complexes of Tc-99m have been used for investigating more parts of the body.

This invention relates to complexes of e.g. technetium-99m useful as diagnostic pharmaceuticals, and in particular to complexes which are capable of crossing the blood-brain barrier and being retained in the brain for a time to permit diagnosis.

European Patent Specification No. 123504 (published on Oct. 31st, 1984) provides a lipophilic macrocyclic complex of Technetium-99m useful as a diagnostic radiopharmaceutical which can be formed by complexing in aqueous solution Tc-99m pertechnetate under reducing conditions with an alkylene amine oxime containing 2 or 3 carbon atoms in the alkylene group, which group is unsubstituted or substituted, the complex having a core with a zero net charge, containing an O—H—O ring closure bond, and being sufficiently stable for parenteral administration and imaging by scintillation scanning, any alkylene substituents present being of the kind useful for adapting radionuclide ligands for body imaging applications. Preferred complexes are believed to have the formula:

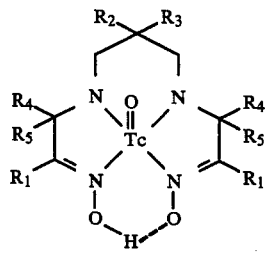

where each $R_1$, $R_4$ and $R_5$ is hydrogen or C1 to C12 alkyl, and each of $R_2$ and $R_3$ is hydrogen, hydroxyl, C1 to C12 alkoxyl, C1 to C22 hydrocarbon which may be alkyl, alkenyl, alkaryl, aralkyl or aryl, or tertiary amine with 1 to 20 carbon atoms, or $R_2$ and $R_3$ form, together with the carbon atom to which they are attached, a cycloaliphatic ggroup which may be amine substituted.

The present invention relates to a group of complexes, falling within the scope of the invention of the aforesaid European patent specification but not specifically described therein, which show interesting properties particularly as regards brain retention.

The present invention provides a lipophilic macrocyclic complex, useful as a diagnostic radiopharmaceutical, of Technetium-99m with a propylene amine oxime having the general formula

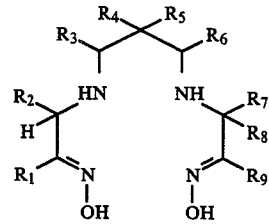

wherein each of $R_1$, $R_2$, $R_3$, $R_4$, $R_5$, $R_6$, $R_7$, $R_8$ and $R_9$ is independently hydrogen, $C_1$–$C_8$ straight- or branched-chain saturated or unsaturated alkyl, aralkyl, aryl, alkoxy, alkoxycarbonyl, alkylcarbonyl, alkylcarbonyloxy, primary secondary or tertiary amine or amide, or nitrile, or one or more of $R_1$, $R_2$; $R_3$, $R_4$; $R_5$, $R_6$; $R_7$, $R_8$; $R_8$, $R_9$ are joined to form a fused or spiro carbocyclic or heterocyclic ring, provided that, when $R_1$ is the same as $R_9$ and $R_2$ is the same as $R_7$, then $R_8$ is not hydrogen.

The complexes are presently believed to have the general formula:

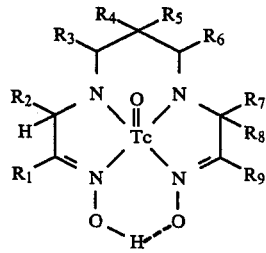

These complexes (and the ligands from which they derive) may have at least one asymmetric carbon atom, namely the carbon atom to which the group $R^2$ is attached. Depending on the nature of $R_3$, $R_4$, $R_5$, $R_6$, $R_7$, and $R_8$, other asymmetric carbon atoms may also be present. As a result many of the ligands show optical isomerism. For instance Compound I (see the Table below) exists in the form of d- and l-enantiomers. Although we have not yet separated and investigated individual stereoisomers, we think it quite possible that the physical and biological properties of the Tc-99m complexes of stereoisomers may differ from one another since such differences have shown up in related complexes. In addition, individual stereoisomers may form two or more technetium complexes, which may have different physical and biological properties. This invention therefore contemplates the propylene amine oxime ligands, and their Tc-99m complexes, both as isomeric mixtures and in the form of one or more of their separated geometrical and stereoisomers.

Each of the aforementioned propylene amine oxime stereoisomers can itself exist in four different isomeric forms by virtue of the restricted rotation about their CN bonds of the two oxime groups. The isomers may have different physical properties (m.pt., b.pt.) and can be separated by chromatographic techniques (TLC and HPLC). Their interconversion is generally facile and is catalysed by mineral or Lewis acids or metal ions. The thermodynamically preferred isomer is expected to be that which provides maximum separation of the bulkier groups. It is probable that the four isomers (of each stereoisomer) may form Tc-99m complexes having different biodistribution properties. The invention therefore contemplates the propylene amine oxime ligands, and their Tc-99m complexes, both in the form of mixtures of the isomers and of individual isomers.

The complexation reaction between the propylene amine oxime ligand and pertechnetate (TcO$_4^-$ from a Mo-99/Tc-99m generator) may be carried out in aqueous or aqueous/organic solution under reducing conditions. Stannous salts are convenient reducing agents, but other reducing agents are well known for this type of reaction and can be used. Since the complexes of this invention contain Tc-99m bound rather strongly, they can alternatively be prepared by a process of ligand exchange. The preparation of Tc-99m complexes by reducing pertechnetate in the presence of a complexing ligand is well-known; the conditions for such general reactions are also well-known and can be used in the particular instance of this invention.

The propylene amine oximes are unsymmetrical about the carbon atom to which groups R$_4$ and R$_5$ are attached and are believed to be in general new compounds. They may be prepared by the general route outlined in the following reaction scheme:

There follows an example of the preparation of a complex according to the invention of technetium-99m with a ligand No. 2 of the above Table.

EXAMPLE 1

1. Preparation of 4,8-diaza-3,3,9-trimethyl-dodecane-2,10-dione bisoxime (i) 3-chloro-3-methyl-2-nitrosobutane (I)

A mixture of 2-methylbut-2-ene (18.5 cm$^3$) and iso-amyl nitrite (19.5 cm$^3$) was cooled to $-10°$ C. Concentrated hydrochloric acid (17.5 cm$^3$) was added at a rate so as to maintain the temperature below 0° C. Stirring was continued for ½ hour after the addition was complete. The precipitate was filtered, washed well with cold ($-20°$ C.) ethanol (4×5 cm$^3$) and dried in vacuo giving the product as a white solid (8.6 g).

(ii) N-(3-Aminopropyl)-1-amino-1,1-dimethyl-2-butanone oxime (II)

A solution of 3-chloro-3-methyl-2-nitrosobutane (25.5 g) in methanol (180 cm$^3$) was added dropwise to a stirred solution of 1,3-diaminopropane (47 cm$^3$) in methanol (75 cm$^3$) at 0° C. After the addition was complete

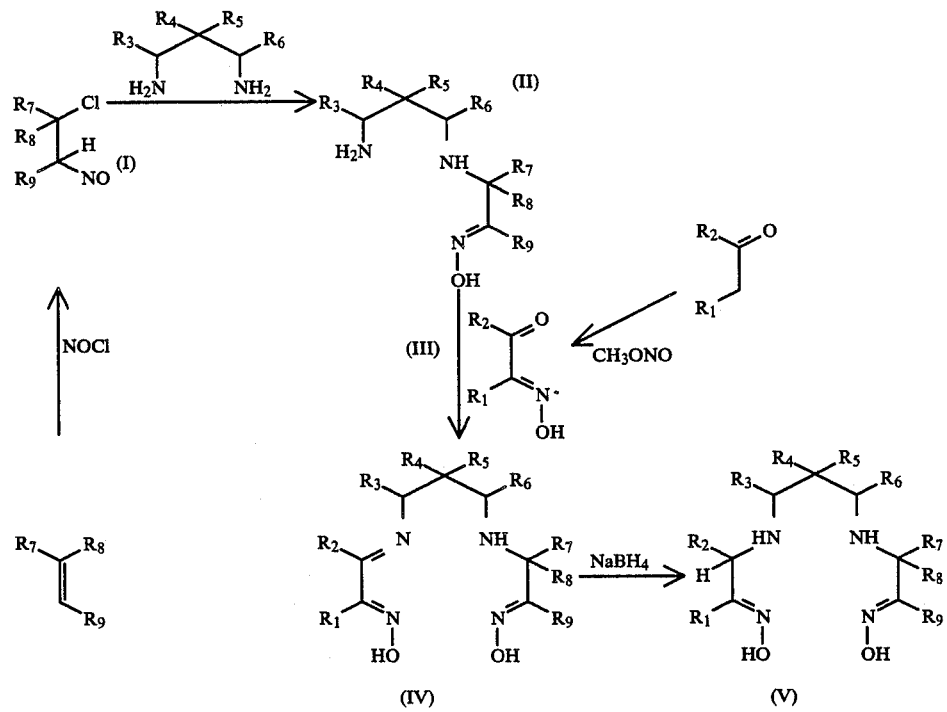

Specific examples of propylene amine oximes that can be used as ligands to make complexes according to this invention are the following:

| No. | R$_1$ | R$_2$ | R$_3$ | R$_4$ | R$_5$ | R$_6$ | R$_7$ | R$_8$ | R$_9$ |
|---|---|---|---|---|---|---|---|---|---|
| 1 | CH$_3$ | CH$_3$ | H | H | H | H | CH$_3$ | CH$_3$ | CH$_3$ |
| 2 | C$_2$H$_5$ | CH$_3$ | H | H | H | H | CH$_3$ | CH$_3$ | CH$_3$ |
| 3 | CH$_3$ | CH$_3$ | H | CH$_3$ | CH$_3$ | H | CH$_3$ | CH$_3$ | CH$_3$ |
| 4 | CH$_3$ | C$_2$H$_5$ | H | CH$_3$ | CH$_3$ | H | CH$_3$ | CH$_3$ | CH$_3$ |
| 5 | CH$_3$ | CH$_3$ | H | H | H | H | CH$_3$ | CH$_3$ | C$_2$H$_5$ |
| 6 | CH$_3$ | C$_2$H$_5$ | H | H | H | H | CH$_3$ | CH$_3$ | CH$_3$ |
| 7 | C$_2$H$_5$ | CH$_3$ | H | H | H | H | CH$_3$ | CH$_3$ | C$_2$H$_5$ |
| 8 | CH$_3$ | CH$_3$ | H | H | H | H | C$_2$H$_5$ | C$_2$H$_5$ | CH$_3$ |
| 9 | i-3$_3$H$_7$ | CH$_3$ | H | H | H | H | CH$_3$ | CH$_3$ | CH$_3$ | the mixture was refluxed for 6 hours. Removal of the methanol in vacuo gave a yellow oil which was slurried in water (50 cm$^3$). The white precipitate was removed by filtration and the pH of the aqueous solution adjusted to about 11. After saturating with salt the solution was continuously extracted with dichloromethane for 36 hours. The organic phase was dried (MgSO$_4$) and concentrated in vacuo giving a yellow oil. Recrystallisation from ether/petrol gave pure product as a white crystalline solid, 9.9 g. Mpt. 69°–72° C.

NMR ($^1$H, 200 MHz, d$_6$-DMSO): 2.58(2H, t, CH$_2$N), 2.24(2H, t, CH$_2$N), 1.70(3H, s, CMe), 1.42(2H, q, CH$_2$), 1.11(6H, s, CMe$_2$)ppm.

(iii) Preparation 2,3-pentanedione-3-oxime (III)

Methyl nitrite was bubbled, at a rate sufficient to maintain vigorous reflux, into a well stirred mixture of 2-pentanone (102 g), ether (400 cm$^3$) and concentrated hydrochloric acid (15 cm$^3$). The methyl nitrite gas was generated by the dropwise addition of a solution of concentrated sulphuric acid (100 cm$^3$) and water (95 cm$^3$) onto a stirred slurry of sodium nitrite (112 g), methanol (66 g) and water (75 cm$^3$). After the addition was complete the mixture was neutralised with saturated aqueous sodium bicarbonate (32 g in 300 cm$^3$). The ether layer was separated and the aqueous layer extracted with more ether. The combined organic layers were dried and concentrated in vacuo giving a yellow oil which crystallised on standing. Recrystallisation from hot hexane gave pure product (67 g), mp 54°–5° C.

(iv) 4,8-Diaza-3,3,9,-trimethyl-dodeca-8-ene-2,10-dione bisoxime (IV)

2,3-Pentanedione-3-oxime (2.0 g) was dissolved in ethanol (4 cm$^3$) at 70° C. 1,3-Diaminopropane-N-(2-methyl-3-butanone)oxime (3.05 g) was added in portions with stirring. Stirring was continued for 15 minutes and then the ethanol was removed in vacuo. Recrystallisation of the residue from dichloromethane/petrol gave the product as a white solid (3.7 g), mp 115°–116° C.

NMR($^1$H, 200 MHz, d$_6$-DMSO): 11.30, 10.31 (each 1H, s, OH), 3.39 (2H, t, CH$_2$N), 2.50(2H, q, N═CCH$_2$), 2.32(2H, t, CH$_2$NH), 1.96(3H, s, N═CCH$_3$ imine), 1.69 (5H, s+m, N═CCH$_3$+CH$_2$CH), 1.11 (6H, s, CMe$_2$), 0.91 (3H, t, CH$_2$CH$_3$) ppm.

(v) 4,8-Diaza-3,3,9-trimethyl-dodecane-2,10-dione bisoxime (V)

4,8-Diaza-3,3,9-trimethyl-dodeca-8-ene-2,10-dione bisoxime (3.5 g) was stirred in 95% aqueous ethanol (33 cm$^3$) at 0° C. Sodium borohydride (0.10 g) was added in portions to the stirred mixture over ½ hour. Stirring was continued for 2 hours at 0° C. and then water (12 cm$^3$) was added. The mixture was stirred well for 2 hours and then the ethanol was removed in vacuo. Water (8 cm$^3$) was added and the pH adjusted to about 11. After saturating with NaCl the aqueous phase was extracted with dichloromethane (5×40 cm$^3$). The combined organic layers were dried (MgSO$_4$) and concentrated in vacuo giving a viscous yellow oil (3.1 g). Recrystallisation from dichloromethane/ether and then dichloromethane/petrol gave pure product (0.78 g), mp 94°–6° C.

2. Preparation of Tc-99m complex of ligand (V)

The following general method was used to prepare Tc-99m complexes. The first step involves the preparation of a solution of the ligand within a pH range of 7.5 to 8.5. Both the physical form and the nature of the ligand will influence the preferred method for the preparation of the solution.

(i) The ligand as a water soluble salt (for example, the mono, di, or trihydrochloride salt). 2 to 3 mg of the ligand is dissolved in 0.5 ml of saline, and the pH of the solution adjusted to be within the desired range by the addition of 0.5 ml of 0.02M sodium bicarbonate solution in saline.

(ii) A water soluble free base. Approximately 2 mg of the ligand is dissolved in 0.5 ml of 10$^{-3}$M HCl, and the pH of the solution adjusted to 7.5 to 8.5 by the addition of 0.5 ml 0.02M sodium bicarbonate solution in saline.

(iii) A free base or salt of the ligand with poor water solubility 2 to 3 mg of the ligand is dissolved in 0.5 ml of ethanol and 0.5 ml of 0.02M sodium bicarbonate solution in saline is added to adjust the pH to the required level.

To the solution of the ligand at the required pH is added 0.2 ml of a saturated solution of stannous tartrate in saline and 0.5 to 1.5 ml of Tc-99m pertechnetate, obtained from a Mo-99/Tc-99m generator system. Analysis of the resultant mixture indicated that reduction of pertechnetate (to a lower oxidation form of technetium), and complexation of the reduced technetium to the ligand is complete after standing at ambient temperature for 10 minutes.

EXAMPLES 2–7

Ligands 1 and 3–7 were prepared by methods corresponding to Example 1. The following melting points were recorded.

| Compound | m.pt. °C. |
| --- | --- |
| 1 | 124–6 |
| 2 | 94–6 |
| 3 | 100–102 |
| 4 | 108–111 |
| 5 | 111–112 |
| 6 | 51–3 |
| 7 | 112–114 |
| 8 | 94–5 |
| 9 | 101–2 |

NMR spectra were recorded in d$_6$-DMSO at 200 MHz. The chemical shifts ($\delta$, ppm), with the integration and multiplicity in parenthesis, are given in Table I:

TABLE 1

| COMPOUND | OH | R$_9$ | R$_{7,8}$ | R$_{4,5}$ | R$_2$ | R$_1$ | CH$_2$N | CHR$_2$ |
| --- | --- | --- | --- | --- | --- | --- | --- | --- |
| 1 | 10.48(1H,brs) 10.37(1H,brs) | 1.70(3H,s) | 1.13(6H,s) | 1.48(2H,m) | 1.07(3H,d) | 1.66(3H,s) | 2.41(2H,t) 2.32(2H,t) | 3.25(1H,q) |
| 2 | 10.35(1H,s) 10.22(1H,s) | 1.69(3H,s) | 1.10(6H,s) | 1.42(2H,m) | 1.05(3H,m) | CH$_2$ 2.20(2H,m) CH$_3$ 1.05(3H,m) | 2.20(2H,m) 2.37(2H,t) | 3.22(1H,q) |
| 3 | 10.34(1H,s) 10.27(1H,s) | 1.70(3H,s) | 1.17(6H,s) | 0.78(6H,s) | 1.07(3H,d) | 1.65(3H,s) | 2.1–2.0 (4H,m) | 3.12(1H,q) |
| 4 | 10.32(2H,brs) | 1.69(3H,s) | 1.11(6H,s) | 0.78(6H,s) | CH$_2$ 1.45(2H,m) CH$_3$ 0.78(3H,m) | 1.62(3H,s) | 2.15–1.95 (4H,brm) | 2.84(1H,brm) |
| 5 | 10.28(2H,brs) | CH$_2$ 2.35–2.25 (2H,m) CH$_3$ 1.02(3H,m) | 1.12(6H,s) | 1.41(2H,m) | 1.03(3H,m) | 1.64(3H,s) | 2.35–2.25 (4H,m) | 3.16(1H,q) |
| 6 | 10.36(1H,s) 10.31(1H,s) | 1.69(3H,s) | 1.10(6H,s) | 1.42(2H,m) | CH$_2$ 1.42(2H,m) CH$_3$ 0.76(3H,t) | 1.62(3H,s) | 2.20(2H,t) 2.33(2H,m) | 2.90(1H,t) |
| 7 | 10.25(1H,brs) 10.19(1H,brs) | CH$_2$ 2.20(2H,m) CH$_3$ 1.01(3H,m) | 1.12(6H,s) | 1.42(2H,m) | 1.03(3H,d) | CH$_2$ 2.20(2H,m) CH$_3$ 1.01(3H,m) | 2.36(2H,t) 2.20(2H,m) | 3.17(1H,q) |
| 8 | 10.39(1H,s) 10.25(1H,s) | 1.67(3H,s) | CH$_2$ 1.43(4H,m) CH$_3$ 0.64(6H,t) | 1.43(2H,m) | 1.05(3H,d) | 1.64(3H,s) | 2.36(2H,t) | 3.17(1H,q) |
| 9 | 10.32(1H,s) | 1.69(3H,s) | 1.10(6H,s) | 1.43(2H,m) | 1.08(3H,d) | CH$_3$ 1.13(6H,d) | 2.24(2H,t) | 3.18(1H,q) |

TABLE 1-continued

| COMPOUND | OH | R9 | R7,8 | R4,5 | R2 | R1 | CH2N | CHR2 |
|---|---|---|---|---|---|---|---|---|
| | 10.16(1H,s) | | | | | CH 2.82(1H,m) | 2.23(2H,t) | |

Abbreviations:
s = singlet
d = doublet
t = triplet
q = quartet
m = multiplet
br = broad Complexes were prepared by the method described in Example 1.

EXAMPLE 8

In Vivo biodistribution studies 0.1 ml of the Tc-99m complex solution is administered by intravenous injection (lateral tail vein) to each of 5 rats (140-220 g). The injected dose is equivalent to approximately 200 Ci of Tc-99m. Three rats are sacrificed at 2 minutes post injection, and the two rats one to two hours post injection. At dissection the organs and tissue samples shown in the following Table are taken, and assayed for radioactivity. The uptake in each organ or tissue is calculated as a percentage of total activity recovered. Results reported in Table II.

BIODISTRIBUTION DATA

TABLE II

| Compound | Sacrifice | % id/organ | | | | |
|---|---|---|---|---|---|---|
| | | Brain | Blood | Muscle | Lung | Liver |
| 2 minute sacrifice | | | | | | |
| 1 | | 1.56 | 8.49 | 51.99 | 2.55 | 19.14 |
| 2 | | 1.24 | 7.57 | 36.50 | 2.45 | 18.06 |
| 3 | | 1.03 | 7.17 | 30.15 | 1.17 | 21.56 |
| 4 | | 1.0 | 4.08 | 23.9 | 1.25 | 11.75 |
| 5 | | 0.62 | 5.38 | 16.77 | 2.18 | 25.27 |
| 6 | | 1.1 | 5.69 | 26.62 | 2.31 | 24.86 |
| 7 | | 1.15 | 7.11 | 30.90 | 3.67 | 20.10 |
| 8 | | 1.10 | 6.26 | 38.27 | 2.46 | 18.36 |
| 9 | | 0.82 | 5.50 | 30.53 | 1.99 | 20.85 |
| 1-2 hour sacrifice | | | | | | |
| 1 | 2 hour | 1.42 | 4.32 | 10.81 | 1.81 | 22.07 |
| 2 | 2 hour | 0.90 | 3.62 | 15.1 | 1.49 | 12.07 |
| 3 | 2 hour | 0.57 | 3.50 | 13.95 | 0.66 | 16.76 |
| 4 | 1 hour | 0.29 | 3.26 | 9.05 | 0.64 | 23.34 |
| 5 | 1 hour | 0.53 | 2.38 | 7.53 | 0.64 | 18.77 |
| 6 | 1 hour | 0.66 | 2.69 | 6.37 | 1.07 | 17.08 |
| 7 | 1 hour | 1.06 | 4.07 | 11.30 | 1.66 | 16.57 |
| 8 | 1 hour | 0.64 | 3.16 | 11.25 | 2.03 | 15.89 |

TABLE II-continued

| Compound | Sacrifice | % id/organ | | | | |
|---|---|---|---|---|---|---|
| | | Brain | Blood | Muscle | Lung | Liver |
| 9 | 1 hour | 0.19 | 3.85 | 6.15 | 0.88 | 24.12 |

The brain retention of these complexes is in general surprisingly superior to that of the complexes described in EP A No. 123504.

I claim:

1. A propylene amine oxime having the general formula

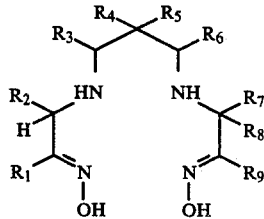

wherein each of $R_1$, $R_2$, $R_7$, $R_8$ and $R_9$ is $C_1$ to $C_4$ alkyl, $R_3$ and $R_6$ are H, and $R_4$ and $R_5$ are H or methyl.

2. A complex of Technetium-99m with a propylene amine oxime, which complex has the formula

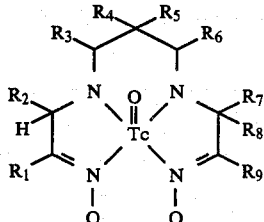

wherein each of $R_1$, $R_2$, $R_7$, $R_8$ and $R_9$ is $C_1$ to $C_4$ alkyl, $R_3$ and $R_6$ are H, and $R_4$ and $R_5$ are H or methyl.

* * * * *